(12) United States Patent
Algotsson et al.

(10) Patent No.: US 9,944,722 B2
(45) Date of Patent: Apr. 17, 2018

(54) CHELATOR AND USE THEREOF

(75) Inventors: Mattias Algotsson, Uppsala (SE); Lars C. Andersson, Uppsala (SE); Eggert Brekkan, Uppsala (SE); Lee Hedemyr, Uppsala (SE); Jean-Luc Maloisel, Uppsala (SE); Ronnie Palmgren, Uppsala (SE)

(73) Assignee: GE Healthcare Bioprocess R&D AB, Uppsala (SE)

( * ) Notice: Subject to any disclaimer, the term of this patent is extended or adjusted under 35 U.S.C. 154(b) by 429 days.

(21) Appl. No.: 13/701,074

(22) PCT Filed: May 30, 2011

(86) PCT No.: PCT/SE2011/050669
§ 371 (c)(1),
(2), (4) Date: Nov. 30, 2012

(87) PCT Pub. No.: WO2011/152782
PCT Pub. Date: Dec. 8, 2011

(65) Prior Publication Data
US 2013/0072638 A1 Mar. 21, 2013

(30) Foreign Application Priority Data
Jun. 1, 2010 (SE) ...................................... 1050551

(51) Int. Cl.
C07C 237/10 (2006.01)
C08B 37/00 (2006.01)
B01J 20/289 (2006.01)
B01J 20/32 (2006.01)
C07C 323/60 (2006.01)
B01J 20/281 (2006.01)

(52) U.S. Cl.
CPC ......... *C08B 37/0039* (2013.01); *B01J 20/281* (2013.01); *B01J 20/289* (2013.01); *B01J 20/3219* (2013.01); *B01J 20/3251* (2013.01); *B01J 20/3265* (2013.01); *C07C 237/10* (2013.01); *C07C 323/60* (2013.01)

(58) Field of Classification Search
CPC .................................................. C07C 237/10
See application file for complete search history.

(56) References Cited

FOREIGN PATENT DOCUMENTS

| EP | 1 199 312 A2 | 4/2002 | |
|----|---|---|---|
| EP | 2 022 561 | 2/2009 | |
| WO | WO 2009/008802 | 1/2009 | |
| WO | 2010/045241 A1 | 4/2010 | |
| WO | 2011038356 | * 3/2011 | ............. C07H 15/02 |

OTHER PUBLICATIONS

European Search Report for EP Application No. 11790086.0 dated Jun. 25, 2015 (9 pages).

Gupta et al., "Design and Development of Integrase Inhibitors as Anti-HIV Agents," Current Medicinal Chemistry, 2003, 10:1779-1794.
Tuntiwechapikul et al., "Design and Synthesis of the G-Quadruplex-Specific Cleaving Reagent Perylene-EDTA Iron (II), " J. Am. Chem. Soc., 2001, 123:5606-5607.
Liu et al., "Diethylene Triamine Pentaacetic Acid, or Ethylene Diamine Tetraacetic Acid, or Amine Triacetate-Modified Porphyrins and Metalloporphyrins, Their Preparation and Application," XP-002740650.
Zhou et al., "Synthesis of Amphiphilic Dimers of Gd(III) Complexes and Their Liver-Selective Contrast Enhancement in MRI," XP-002740651.
Zhou et al., "Synthesis and Relaxivity of Neutral Dimeric Gd(III) Complexes Derived from L-lysine with Long Chain Alkyl Esters," XP-002740652.
Ryabinin, V., et al., Eur. J. Med. Chem., 35 (2000) 989-1000.
Yu, K., et al., Aust. J. Chem., 60 (2007) 218-222.

* cited by examiner

*Primary Examiner* — Noble E Jarrell
(74) *Attorney, Agent, or Firm* — Eversheds Sutherland (US) LLP

(57) ABSTRACT

The present invention relates to dimeric pentadentate chelators with exceptionally strong binding of metal ions, for detection, immobilization and purification of biomolecules. Dimeric chelators offer a cooperativity of binding of two adjacent immobilized metal ions simultaneously to a histidine-tagged biomolecule, which gives advantageous properties regarding strength of binding compared to a corresponding monomer chelator. In addition, a dimer increases the selectivity (ease of separation) against non-tagged biomolecules with low metal-ion affinity.

The dimeric pentadentate chelator according to the invention has the following general formula:

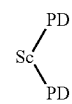

wherein

Sc is a scaffold or a connecting structure that contains at least two functional groups enabling coupling of two pentadentate chelators (PD), and PD is a pentadentate chelator having the formula:

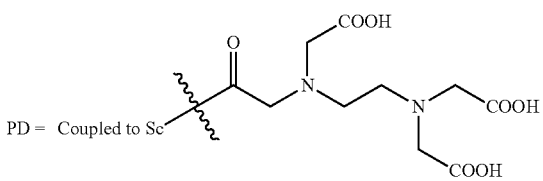

9 Claims, 2 Drawing Sheets

CHELATOR AND USE THEREOF

CROSS-REFERENCE TO RELATED APPLICATIONS

This application is a filing under 35 U.S.C. 371 of international application number PCT/SE2011/050669, filed May 30, 2011, published on Dec. 8, 2011 as WO 2011/152782, which claims priority to application number 1050551-9 filed in Sweden on Jun. 1, 2010.

TECHNICAL FIELD

The present invention relates to the field of biomolecule purification, detection, binding and/or immobilization, and more specifically to methods for preparing and using biomolecule adsorbents and binders in the form of dimeric pentadentate metal-ion chelators, that display unusually strong and EDTA-resistant binding of metal ions.

BACKGROUND

The affinity chromatography method denoted IMAC (Immobilized Metal Ion Affinity Chromatography), pioneered by Porath and coworkers (*Nature* 258:598, 1975), has been in use for protein purification for decades. The principle of IMAC lies in the fact that many metal ions can form coordination bonds between oxygen and nitrogen atoms of amino acid side chains in general and of histidine, cysteine, and tryptophan in particular. The use of IMAC started to increase very considerably in the late 1980:ies with the introduction of methods to genetically modify proteins of interest, so that they contained more histidine residues than coded for by the natural gene, for increased affinity for immobilized metal ions. Such "histidine-tags" can have consecutive His residues, usually 6-10×His, or be various short peptide segments containing His residues together with other amino acid residues (Hochuli et al., *Bio/Technology* 6:1321, 1988; Chaga et al., *J Chromatogr A* 864:247, 1999). A histidine-tag is accordingly used with the aim of giving the recombinant target protein an affinity for immobilized metal ions that is higher or considerably higher than that of any natural protein that can be present together with the non-purified target protein, e.g. in a cell lysate.

Notably, the histidine-tags of such recombinant proteins are not only being used for affinity purification purposes, but also for immobilization of the proteins via immobilized chelators and their metal ions for protein-detection purposes (see Discussion below). It should be mentioned that in all these applications, the use of imidazole as a competitive agent that, at an optimized concentration, decreases unwanted interactions between non-tagged components and metal-ion charged chelators, can be advantageous. This is well known and much used.

Various metal ions have been in use for the purposes here mentioned, notably ions of Ni, Cu, Co, Zn, Ca, Mg, Fe, Ga, Sc and, in medical diagnostics applications with chelator conjugates, radioisotopes of Y, In, Tc, Cu, Ga and others.

Chelators vary in structure and properties, notably in how many of the coordination positions of a metal ion the chelator occupies, or is considered to occupy. Accordingly, chelators can be denoted tri-dentate, tetra-dentate, or pentadentate. This coordination position property of chelators is obviously of importance for the strength of binding of metal ions. Much used and commercialised chelators are imino-diacetic acid (IDA) which is a tri-dentate chelator, and nitrilotriacetic acid (NTA) which is a tetra-dentate chelator.

Pentadentate chelators have been less used, but have been described in the literature, e.g. TED, trislcarboxymethyl) ethylenediamine (Porath & Olin, *Biochemistry* 22:1621, 1983) and IMAC resins with pentadentate chelators are also commercially available.

It should be noted that careful chelator synthesis and, e.g., coupling to a matrix cannot be considered trivial, in case a single homogeneous chelating ligand is desired. Adsorbents/chelators that exist/are prepared as single species, and are not mixtures, are obviously well adapted to show as distinct properties as is possible, to the benefit of the intended use. The non-triviality of preparation of IMAC adsorbents can be especially evident in cases where a ligand is synthesized step-wise in situ, i.e. on a matrix (McCurley & Seitz, *Talanta* 36:341, 1989); see also below. In other cases where a chelator is synthesized in solution and then purified to remove unwanted side products, also the subsequent coupling procedure may need to be performed with skill and experience, to give only a single mode of chelator immobilization.

There are several potential advantages that could be attributed to pentadentate chelators. All protein binding to the complexed metal ion should be weakened compared to tri- and tetra-dentate chelator since the number of metal ion coordination sites available for a biomolecule is lower. Thus, many non-tagged proteins that show some affinity for metal ion complexes with tri- and tetradentate chelators may not bind at all or only weakly, leading to higher selectivity for histidine-tagged proteins. This could be of particular importance for low-level target protein expression, where competitive displacement of weak, unwanted binders by an excess of the strongest binder, namely the histidine-tagged protein, is difficult to use to an advantage at IMAC purification.

Furthermore, the stronger binding of metal ions to a pentadentate chelator will decrease the loss of the ions during chromatography, decrease the risk for contamination of the purified protein with traces of metal ions (which may be harmful to the protein), and make the chromatography resin re-usable without the need for re-charging with new metal ions before the next use. Such aspects are especially important for feeds (=samples applied to the chromatographic column) like animal cell culture media and buffers that are "aggressive", i.e., that tend to remove the immobilized metal ions. Also when substances that disturb the purification by interacting with the metal ions are present in feeds and/or buffers, e.g. some disulfide-reducing agents, it should be an advantage to use IMAC resins that have a pentadentate chelator. Less contamination of work environments and wastewater with released metal ions would also be a consequence of a firm metal ion binding.

Prior Art Related To Monomeric Pentadentate Chelators

Haner et al. (*Analytical Biochemistry* 138:229, 1984) describe pentadentate chelator adsorbents produced by linking EDTA covalently to amino-agarose. A cobalt complex of EDTA was used for coupling to the polymer resin. The described use of the resins was the removal of unwanted $Ca^{2+}$ ions.

Similarly to Haner et al., pentadentate chelators on amine-derivatized non-toxic polymers have been described by Schellenberg et al., Eastern Virginia Medical School, Norfolk, US (U.S. Pat. No. 6,020,373) and by Li et al., Changchun Institute of Applied Chemistry, China (CN 1,966,088). These inventions and the uses thereof were in the fields of medicine and medical diagnostics.

EP 2 022 561 (Gorlich & Frey, Max-Planck-Gesellshaft, Munchen, DE) describes a method for binding of polycarboxylic acids such as EDTA or EGTA, to a solid phase comprising amino groups. It was claimed that single-point binding, i.e., via only one carboxyl group predominated under certain conditions.

Also WO 2009/008802 (Andersson et al., GE Healthcare, Uppsala, SE) relates to easy and rapid coupling of precursors of pentadentate chelators to amine-containing polymers, to give resins with very strong binding of metal ions, which is advantageous for many instances of biomolecule adsorption and/or detection.

Prior Art Related To Di- Or Trimeric Chelators For Binding Of Biomolecules

Thus, all the above publications relate to monomeric pentadentate chelators. There are also several published descriptions of the preparation and use of di-and trimeric chelators holding two or three adjacent metal ions, in the field of immobilization of (histidine-tagged) proteins for interaction studies by surface plasmon resonance analysis or similar analysis, and mostly or exclusively describing NTA-based chelators, i.e. tetradentate chelators. Notable in this field are several publications by Piehler and coworkers, Johann Wolfgang Goethe University, Frankfurt, D E (e.g., Analytical Chemistry 77:1092, 2005; US 2008/0038750) and by Ebright & Ebright et al., Rutgers University, New Brunswick, US (J Am Chem Soc 123:12123, 2001; U.S. Pat. No. 7,371,745).

Surprisingly, we have not found any prior art describing pentadentate dimeric chelators in general, nor any descriptions of pentadentate dimeric chelators that display unusually strong binding of metal ions, nor any use of such chelators for binding to, or adsorbing biomolecules.

SUMMARY OF THE INVENTION

The present invention provides methods to prepare chelators with two adjacent binding sites for metal ions. Each of those sites should be pentadentate in the configuration of the coordination bonds, to maintain the strong metal-ion binding seen in the corresponding monomer chelator. Such non-monomeric chelators could be denoted dimeric chelators. The intention with such a dimeric chelator is to reach a cooperative binding effect, i.e. a much increased affinity in interactions with histidine-tagged biomolecules, compared to the corresponding monomeric chelator, due to a simultaneous binding of the two immobilized metal ions to a single histidine tag. Such a cooperative effect would also increase the binding specificity for histidine-tagged proteins, i.e., the largest increase in affinity would undoubtedly be for proteins with several adjacent His residues, while for most other, non-tagged proteins, the increase in affinity would be less pronounced or none, due to the absence of a histidine-tag.

In a first aspect the present invention relates to a dimeric pentadentate chelator having the following general formula:

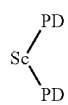

wherein

Sc is a scaffold or a connecting structure that contains at least two functional groups enabling coupling of two pentadentate chelators (PD), and PD is a pentadentate chelator having the formula:

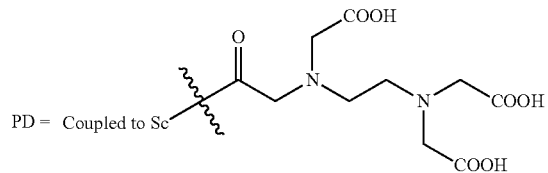

Sc comprises three functional groups in its structure and has the following general formula: $(Z_f)_2$-Sca-$W_f$ before coupling to PD, wherein $Z_f$ and $W_f$ are selected from —OH, —SH or —OCH$_2$CH=CH$_2$, —CO$_2$H, —NH$_2$ or —NH—, —N$_3$, CN, OTs, OMs, Cl, Br, —CHO, —C≡CH or epoxide groups, such that they can be functionalized/derivatized in an orthogonal fashion, and Sca is a straight, branched or cyclic configuration of 2-100 atoms comprising C, N, O, S and H.

Preferably Sc comprises two amine functions in its structure, more preferably Sc comprises three amine functions in its structure and most preferably is derived from diethylentriamine.

Optionally a spacer Sp1 is provided between Sc and the respective PD

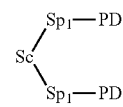

wherein Sp1 has the following formula U—SP—NH$_2$ before coupling to PD and Sc in which U is selected from —OH, —SH or —OCH$_2$CH=CH$_2$, —CO$_2$H, —NH$_2$ or —NH—, —N$_3$, CN, OTs, OMs, Cl, Br, —CHO, —C≡CH or epoxide groups and SP is a straight or branched configuration of 2-100 atoms comprising C, N, O, S and H.

Preferably, the spacer Sp1 is derived from 6-amino hexanoic acid.

In a preferred embodiment, the dimeric pentadentate chelator is provided with a group Q:

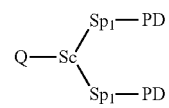

wherein Q is a solid phase, a detection label or a biomarker.

In one alternative, Q is a solid phase comprising a natural or synthetic polymer.

The solid phase may for example be a porous chromatographic support, made of a cross-linked carbohydrate material, such as agarose, agar, cellulose, dextran, chitosan, konjac, carrageenan, gellan or alginate, preferably agarose.

Alternatively, the dimeric pentadentate chelator has a Q made of synthetic polymers such as styrene derivatives, divinylbenzene, acryl amides, acrylate esters, methacrylate esters, vinyl esters or vinyl amides.

For batch chromatography uses, Q of the the dimeric pentadentate chelator may comprise magnetic particles. The magnetic particles may for example be emulgated into a chromatographic support Q.

For detection/analytical uses, Q of the dimeric pentadentate chelator may comprise a sensor surface. The detection/analysis may for example be by SPR (surface plasmon resonance).

Optionally a spacer Sp2 is provided between the scaffold Sc and the group Q:

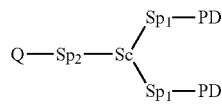

wherein Sp2 has the following formula $X_f$—SP—$Y_f$ before coupling to Q and Sc, in which $X_f$ and $Y_f$ are selected from —OH, —SH or —OCH$_2$CH=CH$_2$, —CO$_2$H, —NH$_2$ or —NH—, —N$_3$, CN, OTs, OMs, Cl, Br, —CHO, —C≡CH or epoxide groups and SP is a straight or branched configuration of 2-100 atoms comprising C, N, O, S and H.

Preferably, $X_f$ is —CO$_2$H and $Y_f$ is —SH.

Preferably, the spacer Sp2 is derived from mercapto hexanoic acid.

In a second aspect, the invention relates to use of the above dimeric pentadentate chelator as a labeling/detection/imaging agent, wherein Q is a detection label or biomarker.

In case of a biomarker, the chelator or its chelated metal or metal ion may be labeled with any suitable label, such as a fluorescent label.

The dimeric pentadentate chelator may also be used as a binding partner, for example immobilized on a sensor surface, such as in SPR applications.

A preferred use is as a chromatography adsorbent/matrix, wherein Q is a chromatography bead, a monolith, a membrane or a filter.

BRIEF DESCRIPTION OF THE DRAWINGS

FIG. 1A shows the result with a column containing 1 ml IMAC resin with Ni$^{2+}$-charged dimeric pentadentate ligand, and FIG. 1B shows the corresponding result with a monomeric pentadentate ligand corresponding to the dimeric one, at approximately the same ligand concentrations.

DETAILED DESCRIPTION AND DISCUSSION OF THE INVENTION

Figure 1A:
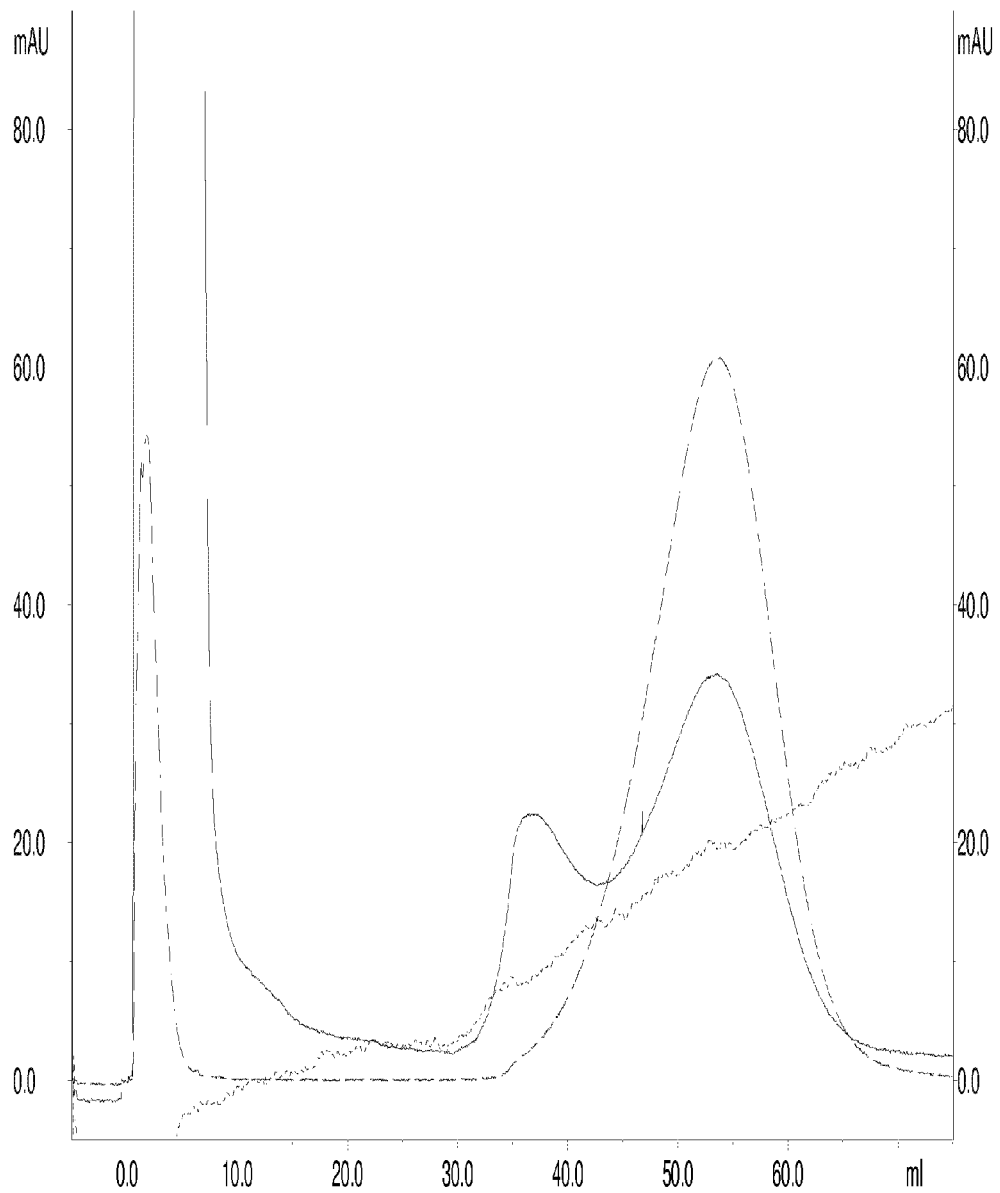
FIGS. 1A and 1B are illustrating Example 5 and show IMAC separations of mixtures of non-tagged E. coli proteins (with absorbance at 280 nm in the elution profile) and histidine-tagged protein EGFP-(His)$_6$ (with absorbance at 280 and 490 nm in the elution profile). Dotted line=conductivity, with a linear increase due to the elution gradient of imidazole applied (y-axis not shown; scale is 49-54 mS/cm). Solid line (with left-hand y-axis)=absorbance at 280 nm; 10 mm light path. Hatched line (with right-hand y-axis)=absorbance at 490 nm; 10 mM light path.

The invention will here be discussed and described more closely, in association with some non-limiting examples.

The dimeric chelators we have prepared and used have the combined advantages of exceptionally strong binding of metal ions and cooperative binding of two adjacent immobilized metal ions to a histidine-tagged biomolecule.

Dimeric chelators with two adjacent binding sites for metal ions were synthesized in solution and purified by preparative reversed phase chromatography. During and after synthesis, the products were characterized by NMR and LC-MS. Covalent coupling of the chelators was done to beaded matrixes (Sepharose™ High Performance) for chromatography, or to Biacore™ sensor chips for surface plasmon resonance analyses of binding of a hexahistidine peptide. The couplings to Sepharose were done without any prior amine-derivatization of the matrix, since this could leave an excess of amines that may give unwanted properties to the resulting product. Initial characterization of the resulting beaded matrixes (IMAC resins) was done by nitrogen elemental analyses (content of chelators) and by a chromatographic and spectrophotometric quantification of the Ni ion capacity and of the loss of bound Ni ions upon exposure to EDTA.

In all chelators here described, the metal ion binding sites were of a design that provides an exceptionally strong, EDTA-resistant binding of Ni ions. This property was confirmed in the characterization of the novel dimeric chelators as a very low loss of bound Ni ions was seen upon prolonged exposure to a high concentration of (free) EDTA, 2 hours with 100 mM.

Examples of Areas of Use of the Invention(s)

Notably, the properties of the invented dimeric chelators, i.e. the combined higher selectivity and affinity for histidine-tagged proteins/biomolecules, compared to corresponding monomeric chelators, and a strong binding of metal ions, will find advantageous use in all fields described below.

Histidine-tags of recombinant proteins are not only being used for affinity purification purposes, but also for immobilization of the proteins via immobilized metal ions and for protein-detection purposes. It should be mentioned that in all these applications, the use of imidazole as a competitive agent that decreases the unwanted interactions between non-tagged components and metal-ion charged chelators, can be advantageous. This is well known and now much used in the areas of working with histidine-tagged proteins. Furthermore, it is obvious that a sufficient strength is needed in a chelator's binding of metal ions. Such a robustness is advantageous from several points of view: E.g., to avoid that traces of free metal ions contaminate purified proteins and possibly cause unwanted protein oxidations, precipitations, etc. Also, avoiding losses of the chelated metal ions from devices like chromatography columns and sensor surfaces is advantageous when wanting to re-use the devices repeatedly. Considerations of losses of metal ions is of particular importance when using samples that contain cell culture media, especially commercial culture media, or samples that contain natural or non-natural compounds that are metal-ion chelators. Chelators in cell culture media (possibly EDTA, free amino acids, etc.) are problematic since they cause losses of the metal ions immobilized in IMAC resins, sensor surfaces and elsewhere. Losses of metal ions can sometimes turn out to be a problem also with more ordinary samples consisting of cell lysates, blood serum and other preparations or samples being of natural or non-natural origin.

1) Affinity purification by IMAC is in widespread use. This is especially the case for histidine-tagged recombinant proteins. A dimeric chelator's combined higher selectivity and affinity for histidine-tagged proteins/biomolecules, compared to corresponding monomeric chelators, will accordingly find wide use. IMAC is also frequently used for purification of non-tagged proteins, which can be over-expressed or coming from natural, non-recombinant sources. Also for such proteins, the use of dimeric chelators, with properties different from the corresponding monomer chelator, might in some instances be put to advantageous use. Strong metal-ion binding is desired.

2) The field of immobilization of histidine-tagged proteins for subsequent studies is large since histidine-tagging is the mostly used way of affinity-tagging recombinant proteins. The studies can be related to finding and characterizing interacting protein partners for a target protein being studied, in investigations within the large area of research on protein-protein complexes, or on protein-protein interactions in the field of signal transduction research. Immobilization of histidine-tagged proteins can also be of use when studying biopharmaceuticals or candidates for biopharmaceuticals, e.g., monoclonal antibodies. Also when investigating and characterizing the interaction of low-Mw substances (drug substances or drug candidates, activators, inhibitors, modulators, etc.) with a target protein, immobilization of that target protein is often used.

Dominant in those fields of need-for-immobilization of histidine-tagged proteins is probably the use of surface plasmon resonance (SPR) analysis with sensor surfaces having bound chelators charged with metal ions. Here, it has been considered that an interaction between a histidine-tagged protein and metal ions bound to common chelators like NTA on sensor surfaces, often is too weak for stable protein immobilization (Nieba et al., *Anal. Biochem.* 252: 217, 1997). This problem has been addressed by investigating di- and trimeric chelators, notably di-NTA and tri-NTA (see, e.g., Lata & Piehler, *Anal. Chem.* 77:1096, 2005). Apart from sensor surfaces in SPR applications, also matrices in the form of beads, membranes or monoliths can find use for immobilization of histidine-tagged proteins via a coupled chelator. Again, after immobilizing the histidine-tagged target protein, the prepared beads/membranes/monoliths can be used for finding and characterizing interaction partners of various kinds 3) A third field of use of metal-ion chelators is detection and quantification of histidine-tagged proteins. Then the metal-ion charged chelator and the histidine-tagged protein often are in free solution, or the histidine-tagged protein is in media such as electrophoresis gels or on so called western blotting membranes, and the metal-ion charged soluble chelator is added for the detection of that protein. In such methods for detection and quantification, one uses in most instances fluorescence-labelled chelators. Other modes of labeling can also be used—radioactive, possibly enzymatic, etc. The detection and quantification can be made after removing an excess of chelator, and leaving for the subsequent detection only the chelators that have found and bound to their histidine-tag target. Alternatively, in a single solution, fluorescent chelators that have bound to their histidine-tagged target can be distinguished from the fluorescent chelators that remain unbound, by methods like fluorescence anisotropy, where the translational and rotational freedom of a fluorescent substance is detected and being accounted for in the analyses.

Such specific detection and quantification of histidine-tagged proteins is useful in the screening for optimal protein expression conditions done by, e.g., analysing a series of lysates from cells grown under different conditions, or a series of lysates from cells with different properties. Here, the absolute or relative concentrations or amounts of histidine-tagged proteins are determined, sometimes with the aid of a calibration curve prepared with known concentrations of the histidine-tagged protein.

Detection of a histidine-tagged protein by the use of a fluorescent or otherwise labeled chelator can also be used during purification procedures to follow the protein of interest and determine the recoveries of the protein during the purification steps. This can be done either by analysing discrete sample fractions collected during, e.g., chromatographic purification, but also by on-line chromatographic monitoring of, e.g., fluorescence in cases where the histidine-tagged protein has been labeled with the chelator prior to a chromatographic procedure.

Similar approaches allow the characterization of a histidine-tagged protein during, e.g., size exclusion chromatography: with the use of chelator labeling, the localization can be accomplished of a histidine-tagged protein in an on-line recorded fluorescence elution profile of such a size-separation, or in eluted discrete fractions. This will give important information about whether the protein is present in a single monomeric form, and/or is present as oligomers or aggregates. Obviously, conditions like pH and ionic strength, etc. can be varied with the aim of, e.g., decreasing the amount of aggregates, and the above outlined method of characterization can then be applied for analysing the success of the changes in conditions.

4) A fourth way of using metal-ion chelators, partly overlapping the detection field as it is described above, is in the (covalent) attachment of chelators to biomolecules, or to simpler natural or non-natural polymers, or to low-Mr compounds. Such conjugates, with metal ions bound to the chelator part of the conjugate, can for instance be used to reversibly attach a histidine-tagged protein to the conjugate. Upon treatment of such a ternary complex with, e.g. imidazole, it dissociates. Such a reversability regarding the binding of the histidine-tagged component can be useful in several instances. Chelator-biomolecule/polymer conjugates could also be used in medical diagnostics (in vivo or in vitro) and related areas, and in clinical treatment. An example of such use is if the conjugate consists of a tumour-specific monoclonal antibody and an attached chelator bearing metal ions that are radioactive. In effect, the antibody is accordingly labeled for ease of detection after having reached its binding site. In addition to detection, the properties of the metal ions, the antibody itself, or the conjugate could infer a therapeutic potential. Undoubtedly, the use of dimeric chelators bearing two metal ions, instead of monomeric, will give the opportunity of labeling to higher densities. And, as already mentioned, a very strong binding of metal ions to the chelator will increase the usability of the corresponding conjugates.

The dimeric pentadentate chelator of the invention has the following general formula:

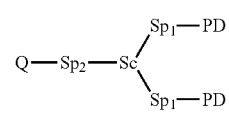

Q = Solid surface, porous material,
detection label or biomarker
Sp$_1$ = Spacer 1
Sc = Scaffold
Sp$_2$ = Spacer 2

PD = Coupled to Sp$_1$

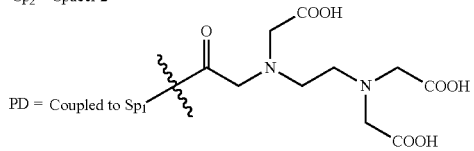

The group Q may comprise of any natural or synthetic polymer. Q may be porous or non-porous and made from any suitable material. In one embodiment the carrier is made of a cross-linked carbohydrate material, such as agarose, agar, cellulose, dextran, chitosan, konjac, carrageenan, gellan, alginate etc. The support is easily prepared according to standard methods such as inverse suspension gelation or obtained as a commercially available product. Carbohydrate carriers, like agarose, are commonly activated before coupling. The activation could be made with standard methods, such as allyl activation using allylglycidyl ether, amino activation, epoxy activation etc. Thus, in one embodiment, Q is a carbohydrate carrier which has been allyl activated before the coupling of the ligand. There is also a possibility to use some form of surface extender, like for example dextran, which could be coupled to the support and then used for coupling of the ligand. Alternatively, Q is made of synthetic polymers such as styrene derivatives, divinylbenzene, acryl amides, acrylate esters, methacrylate esters, vinyl esters, vinyl amides etc. Q could also be magnetic.

In an alternative embodiment the carrier is present on sensor chips or sensor surfaces which monitor protein interactions, like for example a Biacore™ chip.

Alternatively, Q is a detectable labeling agent or a biomarker that could be used for following protein interactions, etc.; for example a fluorescent or radioactive molecule, or an antibody or other biomolecule.

In a preferred embodiment Q are agarose beads.

The spacer 2 (Sp$_2$) has the following general formula: X—SP—Y after coupling to Q and Sc.

The spacer 2 (Sp$_2$) before coupling, is composed of an SP part comprising at least 2 atoms and with reactive groups (Xf, Yf), for coupling to the carrier and to the scaffold.

In the general formula, X is the product of the reaction of a functional group Xf, with Q according to conventional covalent coupling methodologies including also techniques to be developed in the future.

The functional group Xf can for example be any suitable nucleophilic group, any suitable group that can react with a nucleophilic group, any suitable electron rich group or electron poor group that enables the coupling of the ligand to Q. Conventional coupling chemistries are for example reactions with activated carboxylic groups or other activated sp2 carbons, opening of epoxides, substitution reactions, reductive amination, disulfide formation, radical additions and cycloadditions. Thus, in an illustrative embodiment, the functional group Xf is selected from a group such as —OH, —SH, —OCH$_2$CH=CH$_2$, —CO$_2$H, —NH$_2$, —NH—, —N$_3$, —CN, —OTs, —OMs, —Cl, —Br, —CHO, —C≡CH or an epoxide. In an advantageous embodiment, Xf is —SH.

In a similar fashion in the general formula, Y is the product of the reaction of a functional group Yf, with the scaffold (Sc) according to conventional covalent coupling methodologies including also techniques to be developed in the future. In an illustrative example the functional group Yf can be chosen from a similar list of functional group as described for the functional group Xf.

In an advantageous embodiment, Yf is a carboxylic group.

As it is understood by somebody of the art, and according to the choice of the coupling chemistry to Q and to Sc, X and Y can be different or identical. It is also understood that to be able to achieve such structures, the use of activation methods and conventional protection groups methodology should also be considered.

Typically the SP part of the spacer 2 comprises a straight, branched or cyclic hydrocarbon group. The carbon chain may be interrupted at one or more locations by an ether group or some other group, such as thioether, amide, ketone or sulfonamide that can withstand the conditions a chelator may be subjected to during conventional use. In another embodiment the presence of more easily hydrolyzed groups such as ester functions or disulfide groups can also be advantageously used. As understood by the skilled person, the length (size) and the optimal composition of the spacer will depend on several factors, such as the nature of Q, the presence of extender, the structure and size of the ligand, the tagged proteins and the chromatographic application.

In an advantageous embodiment the length of the SP part of the spacer is 2-100 atoms comprising C, N, O, S and H.

In a preferred embodiment the spacer 2 (Sp$_2$) is formed from mercapto hexanoic acid.

The scaffold (Sc) has the following general formula: Z$_2$Sca-W after coupling to Sp1 and Sp2.

The scaffold (Sc) is a connecting structure that contains at least three functional groups (Zf, Zf and Wf) that enables the coupling of two spacers (Sp1 or derived Sp1-PD) at the same time, and the coupling of another different spacer 2 (Sp2) in an orthogonal fashion. This orthogonal functionalization can for example be obtained by the use of two different reactive groups, but in case Z and W are similar groups this can also be obtained using selective protection or reaction taking advantage of differences in reactivity, or the use of non stochiometric ratios of reagents, as it is well known by someone of the art. It is also understood that the choice of the functional group is also directed by the choice of the functional groups on Sp1 and Sp2 to be able to prepare the covalent linkages Z and W.

In such fashion, it is clear for somebody of the art that there are a large number of combinations of orthogonal chemistries that can be applied to achieve the desired construction.

Thus, in an illustrative embodiment, the functional groups Z$_f$ and W$_f$ are selected from a group such as —OH, —SH or —OCH$_2$CH=CH$_2$, —CO$_2$H, —NH$_2$ or —NH—, —N$_3$, —CN, —OTs, —OMs, —Cl, —Br, —CHO or an epoxide. In an advantageous embodiment the scaffold bears two amine groups and one other functional group chosen from the examples above. In a preferred embodiment the scaffold bears three amine groups for coupling to the Sp1 and Sp2.

The core of the scaffold (Sca) is a connecting structure that bears at least three functional groups. Typically Sca comprises a straight, branched or cyclic hydrocarbon group saturated or not. The carbon chain may be interrupted at one or more locations by an amine group, an ether group or some other group, such as thioether, amide, ketone or sulfonamide that can withstand the conditions a chelator may be subjected to, during a conventional use. The carbon chain may also be interrupted at one or more locations by a combination of these groups. The core of the scaffold Sca can also be an aromatic or a heterocyclic group. The functional groups can be, part of the main structure, a substituent of the main structure or in similar fashion part of one of the branches. In an advantageous embodiment Sca has a structure that contains 2-100 atoms comprising C, N, O, S and H.

In a preferred embodiment the scaffold is diethylenetriamine.

The spacer 1 (Sp1) has the following general formula: U—SP—NH$_2$ before coupling.

The spacer 1 (Sp1) is a carbon chain with reactive groups at the ends for coupling to the scaffold and to the pentadentate ligand (PD). Typically the SP part of the spacer comprises a straight, branched or cyclic hydrocarbon group. The carbon chain may be interrupted at one or more locations by an ether group or some other group, such as thioether, amide, ketone or sulfonamide that can withstand the conditions a chelator may be subjected to, during a conventional use. In an advantageous embodiment the spacer SP is a linear structure composed of up to 2-100 atoms comprising C, N, O, S and H.

The reactive group U is chosen to react with Wf in order to attach the Sp1 to the scaffold. In an illustrative example U is selected from —OH, —SH or —OCH$_2$CH=CH$_2$, —CO$_2$H, —NH$_2$ or —NH—, —N$_3$, —CN, —OTs, —OMs, —Cl, —Br, —CHO an epoxide or other functional groups compatible with the chemistry described for Wf. In an advantageous embodiment U is an amine group. In a preferred embodiment U is a carboxyl group.

The coupling between the spacer 1 and the pentadentate ligand (PD) forms an amide linkage. In a preferred embodiment the spacer 1 is derived from 6-amino hexanoic acid. In an alternative embodiment there is no spacer 1 and PD is instead coupled directly to the scaffold.

Synthesis of Ligand Sp2-Sc-(Sp1-PD)2:

In one preferred embodiment all synthetic steps of the ligand preparation are performed in solutions and the ligand is purified previous to coupling to the group Q, enabling a chelator with a unique, uniform and well-defined immobilized structure.

This can be achieved following two main strategies. In a first approach the spacer Sp2 is coupled first with W and then Sp1 and PD are coupled in sequence or as a preformed entity (Sp1-PD). In a second approach Sp1-PD or Sp1 and PD in sequence, are first coupled with Z and the Sp2 is coupled to W.

The sequential introduction of the different spacers and chelating groups is based on the use of orthogonal coupling chemistry, the use of selective protecting groups and selective deprotection procedure or the advantageous utilization of difference of reactivity between similar functional groups, as is easily understood by somebody of the art.

In one preferred embodiment the sequence of reaction is based on the selective coupling of Sp1-PD on a scaffold containing two primary amines and in the presence of a non-protected less reactive secondary amine that is further utilized to introduce the spacer Sp2 under more drastic conditions. Thus, in an illustrative embodiment, the primary amine groups of diethylenetriamine form selectively some amide bonds with a carboxy-containing Sp1-PD yielding a product that can be further functionalized with a carboxy-containing spacer Sp2.

Here follows some non-limiting examples of dimeric pentadentate chelators and their use.

EXAMPLE 1

Synthesis, Coupling and Characterization of a Dimeric Pentadentate Chelator (1)

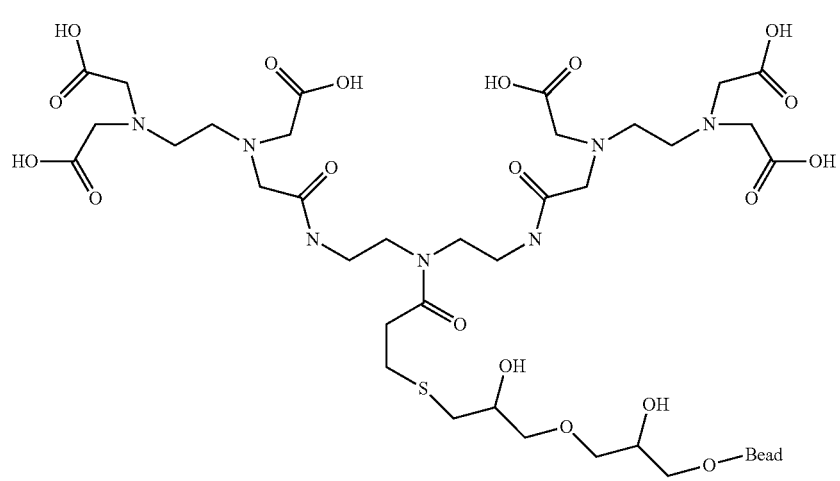

The synthetic route for the pentadentate dimer prototype (1) is described below.

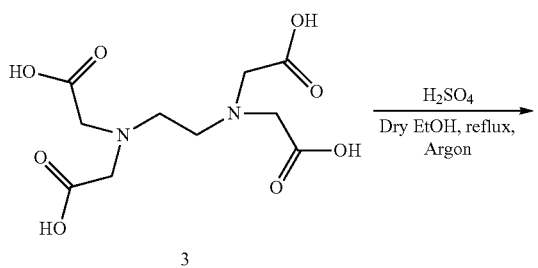

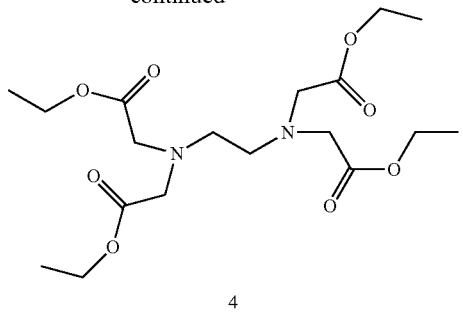

4

Synthesis of the Tetraethyl EDTA Ester (4)

All glassware was dried before use. A 500 ml two-necked round bottomed flask was connected to a water cooler and sealed. 5.0 g (17 mmol) Ethylenediaminetetraacetic acid (3) was added to the flask and dissolved in 200 ml dry ethanol. The flask was flushed with argon and resealed. 3.2 ml (63 mmol) concentrated Sulfuric acid was added to the slurry in one portion. The reaction was refluxed for 17 hours at 90° C. under argon atmosphere. The reaction was monitored by LC-MS (3-100% Acetonitrile (0.05% TFA) in MilliQ water (0.05% TFA), 10 min, 0.5 ml/min, YMC-Pack Hydrosphere C18, S-3 µm, 120 Å, 50×4.6 mm i.d.).

150 ml water was added followed by solid Sodium hydrogen carbonate to pH 9. Ethanol was removed by vacuum and the aqueous solution was extracted with 150 ml Chloroform three times. The organic phases were combined and dried with Magnesium sulfate. The drying agent was removed by filtration and the supernatant was concentrated by vacuum affording 6.3 g (98%) of white crystals.

ESI-MS: m/z=405.2 [M+H$^+$]

phosphate, 6 mM Potassium dihydrogen phosphate, pH 8.0) in a three necked round bottomed flask. 61 µl (16.5 mg/ml, 72 units/mmol) of Pig Liver Esterase solution was added in one portion. A mechanical rotor at 80 rpm applied gentle stirring. The reaction mixture was stirred at 27° C. for 8 hours. The reaction was monitored by LC-MS (3-100% Acetonitrile (0.05% TFA) in MilliQ water (0.05% TFA), 10 min, 0.5 ml/min, YMC-Pack Hydrosphere C18, S-3 µm, 120 Å, 50×4.6 mm i.d.). The reaction mixture was extracted with 3 ml n-Hexane and five times with 10 ml Dichloromethane. Sodium chloride was added to the aqueous phase until saturated then extracted five times with 10 ml Dichloromethane. The organic phases were combined and dried over Magnesium sulfate. The drying agent was removed by filtration and the supernatant was concentrated by vacuum, affording 0.63 g (68%) of amber oil.

ESI-MS: m/z=377.1 [M+H$^+$], 399.1 [M+Na$^+$]

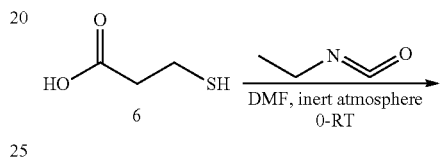

Synthesis of 3-Ethylcarbamoylsulfanyl-Propionic Acid (7)

9.4 ml dry Dimethylformamide was added to a capped 50 ml round bottomed flask under Nitrogen atmosphere. 821 µl (9.4 mmol) of 3-Mercaptopropionic acid (6) was added in one portion via syringe. The solution was cooled to −20° C. 0.82 ml (10.4 mmol) of Ethylisocyanate was added dropwise and the reaction mixture was left to react at room temperature for 18 hrs. The reaction was monitored by TLC. 0.5 g Ce(IV)(SO4)$_2$ and 2.5 g (NH$_4$)$_6$Mo$_7$O$_{24}$ in 5 ml Sulfuric acid and 45 ml deionized water was used as dyeing agent.

The solvent was removed by vacuum, triturated with ether to give white crystals. The crystals were dried affording 1.6 g (98%).

TLC (10:1 Dichloromethane:Methanol, 1% TFA): R$_f$=0.40

Synthesis of the TriethylEDTA ester (5)

1.0 g (2.47 mmol) of the Tetraethyl EDTA ester (4) was suspended in 75 ml buffer (184 mM Sodium hydrogen

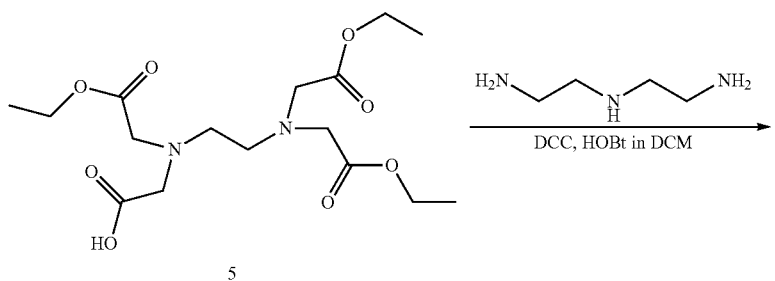

Synthesis of the Secondary Amine (10)

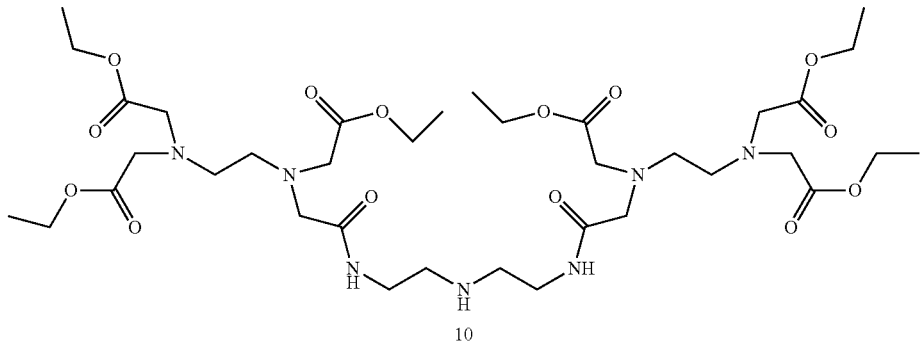

1.0 g (2.7 mmol) triethyl EDTA ester (5) was dissolved in 10.7 ml dry Dichloromethane. 0.44 mg (3.3 mmol) 1-hydroxybenzotriazole hydrate and 0.61 mg (2.9 mmol) N,N'-Dicyclohexylcarbodiimide were added to the solution. The reaction was left to stir for 1 hour at room temperature. 0.14 ml (1.3 mmol) of Diethylenetriamine was dissolved in 3 ml dry Dichloromethane added and the solution was added drop-wise. The reaction left to stir at room temperature for 17 hours. The reaction was monitored by LC-MS (3-100% Acetonitrile (0.05% TFA) in MilliQ water (0.05% TFA), 10 min, 0.5 ml/min, YMC-Pack Hydrosphere C18, S-3 μm, 120 Å, 50×4.6 mm i.d.).

Formed precipitation was removed by filtration and the supernatant was concentrated under vacuum to give crude as amber oil.

The oil was dissolved in minimal amount of Acetonitrile. Formed precipitation was removed by filtration and the supernatant was concentrated to a few milliliter and purified by semi-preparative HPLC (3-100% Acetonitrile (0.05% TFA) in MilliQ water (0.05% TFA) over 10 min, 50 ml/min, C18 column (ACE 10 AQ A 8257 250×30 mm i.d., 10 μm, 100 Å), UV-detection at 214 nm. Collected fractions were combined and concentrated under vacuum until a few milliliters remained. The solution was freeze-dried affording 0.40 g (53%) of light yellow oil.

ESI-MS: m/z=820.4 [M+H$^+$], 842.4 [M+Na$^+$], 410.7 [M+2H$^+$]

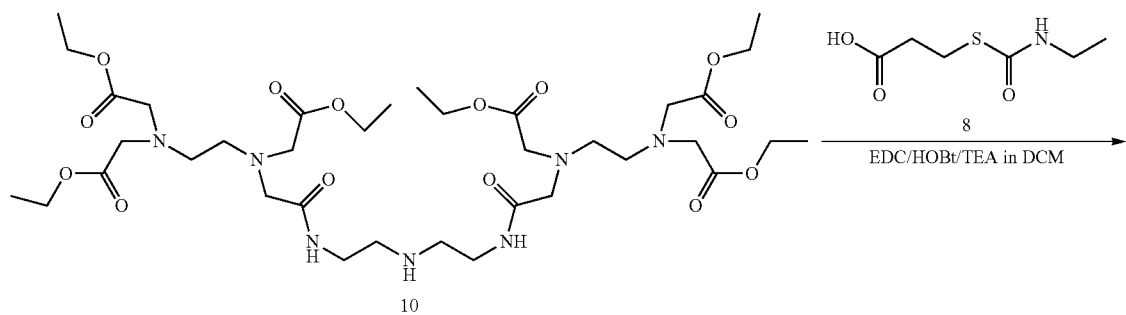

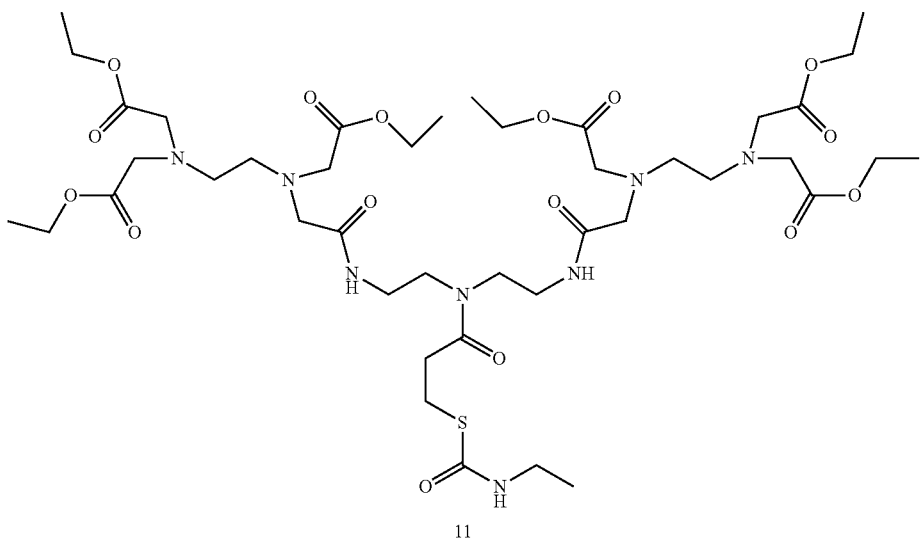

Synthesis of Fully Protected Pentadentate Dimer (11)

0.57 mmol of Ethylcarbamoylsulfanyl acid was dissolved in 3 ml dry Dichloromethane. 0.11 g (0.6 mmol) N-(3-Dimethylaminopropyl)-N'-ethylcarbodiimide hydrochloride and 0.09 g (0.64 mmol) 1-hydroxybenzotriazole hydrate was added and the reaction mixture was left at room temperature for 1 hr. The secondary amine (10) was dissolved in 1 ml dry Dichloromethane and 0.20 µl (1.4 mmol) Triethylamine. The amine solution was added to the reaction mixture drop-wise and the reaction was left at room temperature for 17 hours. The reaction was monitored by LC-MS (3-100% Acetonitrile (0.05% TFA) in MilliQ water (0.05% TFA), 10 min, 0.5 ml/min, YMC-Pack Hydrosphere C18, S-3 µm, 120 Å, 50×4.6 mm i.d.).

The reaction mixture was washed with equal volume of distilled water. The aqueous phase was extracted twice with Dichloromethane. The organic phases were combined and washed with equal volume of 0.1 M Hydrogen chloride solution. The aqueous phase was extracted twice with Dichloromethane. The organic phases were combined and washed with equal volume of saturated Sodium chloride solution. The aqueous phase was extracted twice with Dichloromethane. The organic phases were combined and dried with Magnesium sulfate. The drying agent was removed by filtration and the supernatant was concentrated by vacuum to give crude product as amber oil. The crude was dissolved in 1.5 ml Acetonitrile and purified on semi-preparative HPLC (3-100% Acetonitrile (0.05% TFA) in MilliQ water (0.05% TFA) over 10 min, 50 ml/min, C18 column (ACE 10 AQ A 8257 250×30 mm i.d., 10 µm, 100 Å), UV-detection at 214 nm. Collected fractions were combined and concentrated under vacuum until a few milliliters remained. The solution was freeze-dried affording Pentadentate dimer as light yellow oil.

Protected Pentadentate Dimer (11)

Yield: 40%

ESI-MS: m/z=979.5 [M+H$^+$], 490.3 [M+2H$^+$], 1001.4 [M+Na$^+$]

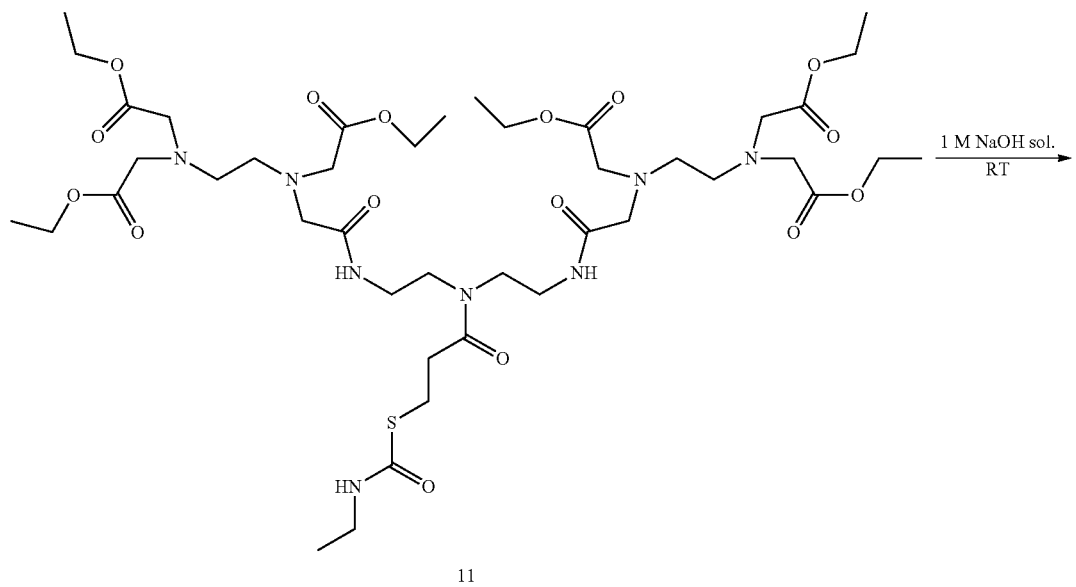

11

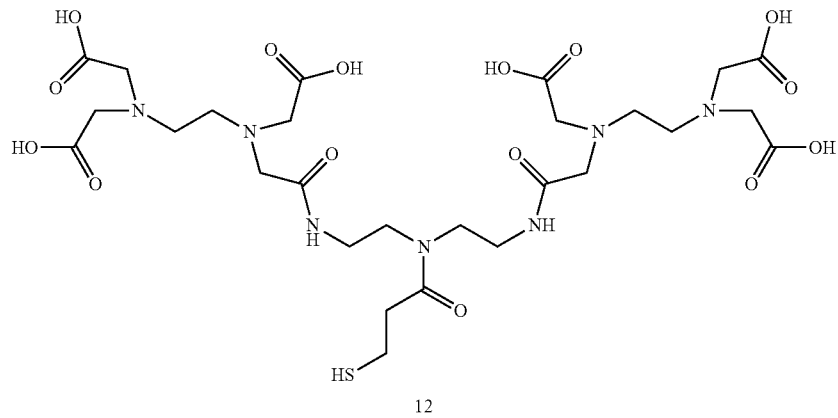

12

Synthesis of the Pentadentate Dimer Ligand (12)

The dimeric pentadentate ligand (11) from above (160 mg, 163 umol) was put in a flask together with sodiumhydroxide (2.0 ml, 1M-solution) and magnetic stirring was begun. After three hours of stirring none of the starting material (11) was seen on LC-MS. The solution was then transferred to a Falcon tube for coupling to allylactivated Sepharose™ HP media.

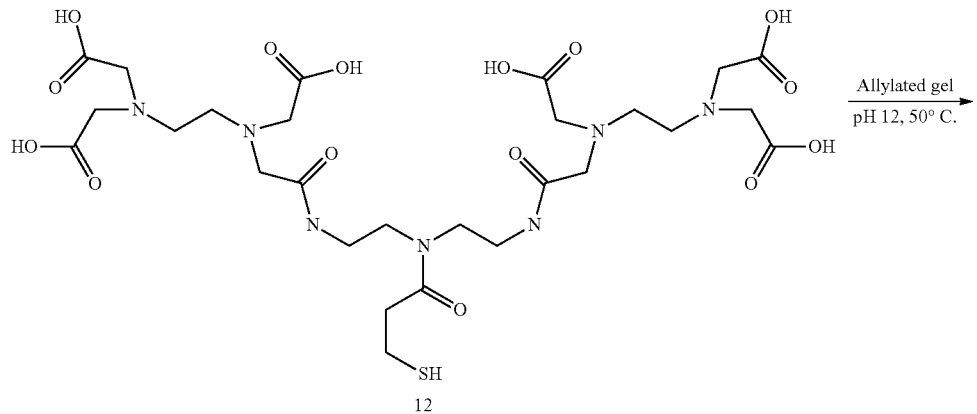

12

-continued

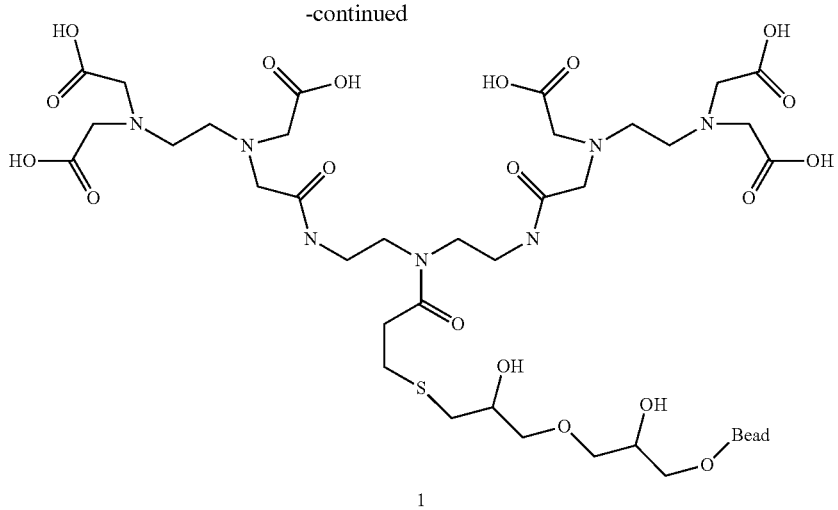

1

Coupling to Allyl Activated Sepharose™ HP Resins to Afford the Dimeric Pentadenate Chelator (1)

Coupling to Allyl Activated Sepharose™ HP Media to Afford a Resin with the Dimeric Pentadentate Chelator (1)

Drained allyl activated (130 μmol allyl/mL resin) Sepharose™ HP resin (3 ml, 0.39 mol) was transferred to a beaker and water (approximately 50 ml) was added to the gel. During vigorous overhead stirring bromine water was added to a consistent yellow colour. After about 5 minutes of stirring sodium formiate was added until the gel slurry was completely discoloured and then left stirring for about 15 minutes. The gel was then transferred to a glass filter and washed with distilled water (50 ml).

The gel was drained and then transferred to the aforementioned Falcon tube with the pentadentate ligand solution (12). Hydrochloric acid (1 ml, 1M-solution) was added to the tube and the pH was then adjusted to 12 with sodium-hydroxide (1M-solution). The tube was then put on a shaking table at 50° C. over night. After about 20 hours the reaction was stopped and the resins washed with distilled water (4×50 ml) on a glass filter.

The dry weight of the resin was determined to 64 mg/ml by drying 0.5 ml of gel on a drying scale and the nitrogen content was then determined by elemental analysis to 0.88% which corresponds to a ligand content of about 6 μmol/ml.

$Ni^{2+}$-binding capacity measurements by frontal analysis, and determination of loss of bound Ni ions. The resin was packed in a chromatography column (e.g. Tricorn™ 5/50) with a bed dimension of approximately 50×5.0 mm (approximately 1 ml); final packing flow was 2 ml/min. The column was attached onto a chromatography system (ÄKTA 10 XT, GE Healthcare). 5.0 mM $NiSO_4$ solution was eluted through the UV detector cell (10 mm cell, detection at 372 nm), bypassing the column, at a flow-rate of 1 ml/min. The absorbance for 5 mM $NiSO_4$ was noted. The column was equilibrated with 5 column volumes (cv) of 20 mM Na-phosphate, 500 mM NaCl, pH 7.4 solution, washed with 5 cv of pure water and then loaded with an excess (30 ml) of 5 mM $NiSO_4$ solution at 1 ml/min. The breakthrough of Ni ions was monitored when reaching saturation and the so called Qb10% value (quantity bound at 10% of the absorbance of the 5 mM $NiSO_4$ solution) was determined. After the loading of Ni ions, the excess of Ni ions was washed out with 10 cv of pure water followed by a wash with 5 cv of 500 mM NaCl to remove loosely bound Ni ions. The column was then washed with 5 cv of 100 mM EDTA, 20 mM Na-phosphate, 500 mM NaCl, pH 7.4 solution and the pump was stopped for 2 hours. After 2 hours, a further 20 cv of 100 mM EDTA, 20 mM Na-phosphate, 500 mM NaCl, pH 7.4 solution was pumped through the column. The amount of washed-out Ni ions in the 500 mM NaCl solution step and the amount of desorbed Ni ions with EDTA solution was determined by integrating the UV peaks at 372 nm generated by the NaCl and EDTA washings (the latter before and after the 2 hour pump stop) followed by quantification using separate calibration curves from application of known amounts of Ni ions in NaCl, or EDTA, respectively. The results were combined with the exact volume of the packed bed in the column, to give μmol $Ni^{2+}$/ml of packed bed of resin.

$Ni^{2+}$-binding capacity (Qb10%): 19 μmol/ml resin.

Amount of $Ni^{2+}$ ions released in the NaCl wash: 3 μmol/ml.

$Ni^{2+}$-content after NaCl wash: 16 μmol/ml resin.

The amount of $Ni^{2+}$ ions released in the 100 mM EDTA eluate after 2 hours of incubation was 0.7 μmol/ml (=4.4% of 16 μmol/ml).

EXAMPLE 2

Synthesis, Coupling and Characterization of a Dimeric Pentadentate Chelator (2)

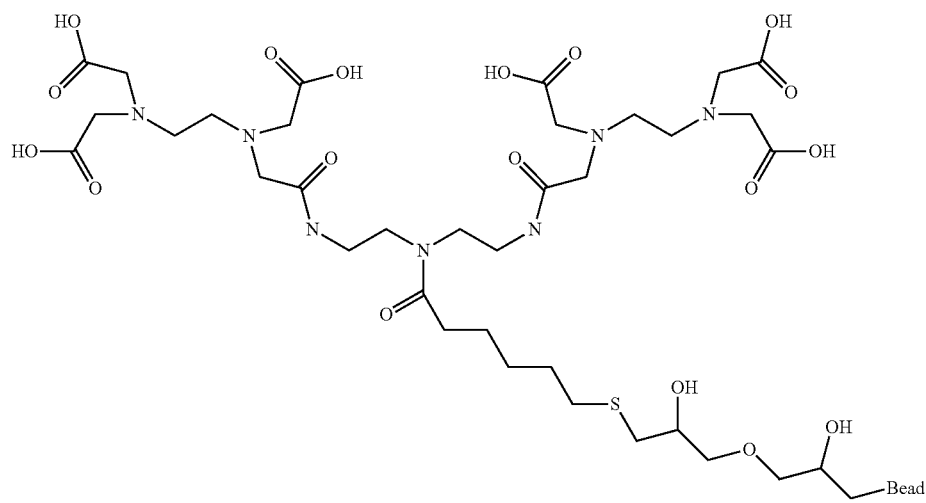

The synthetic route for the pentadentate dimer prototype (2) is described below.

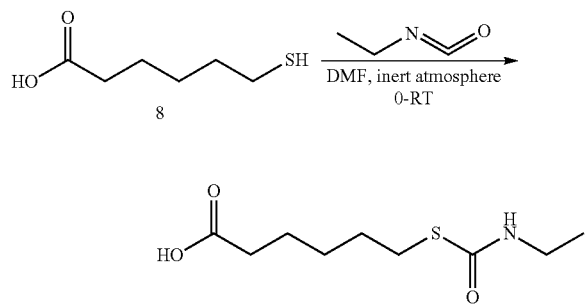

Synthesis of 6-Ethyl Carbamoylsulfanyl-Hexanoic Acid (9)

3.4 ml dry Dimethylformamide was added to a capped round bottomed flask under Nitrogen atmosphere. 294 µl (3.4 mmol) of 3-Mercaptohexanoic acid (8) was added in one portion via syringe. The solution was cooled to −20° C. 294 µl (3.7 mmol) of Ethylisocyanate was added drop-wise and the reaction mixture was left to react at room temperature for 18 hrs. The reaction was monitored by TLC. 0.5 g $Ce(IV)(SO4)_2$ and 2.5 g $(NH_4)_6Mo_7O_{24}$ in 5 ml Sulfuric acid and 45 ml deionized water was used as dyeing agent.

The solvent was removed by vacuum, triturated with ether to give white crystals. The crystals were dried, affording white crystals.

TLC (20:1.5 Dichloromethane:Methanol, 0.5% TFA): $R_f$=0.30

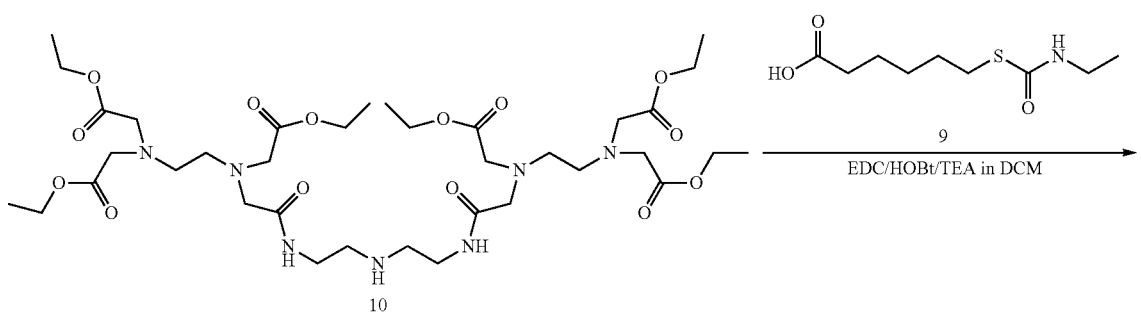

-continued

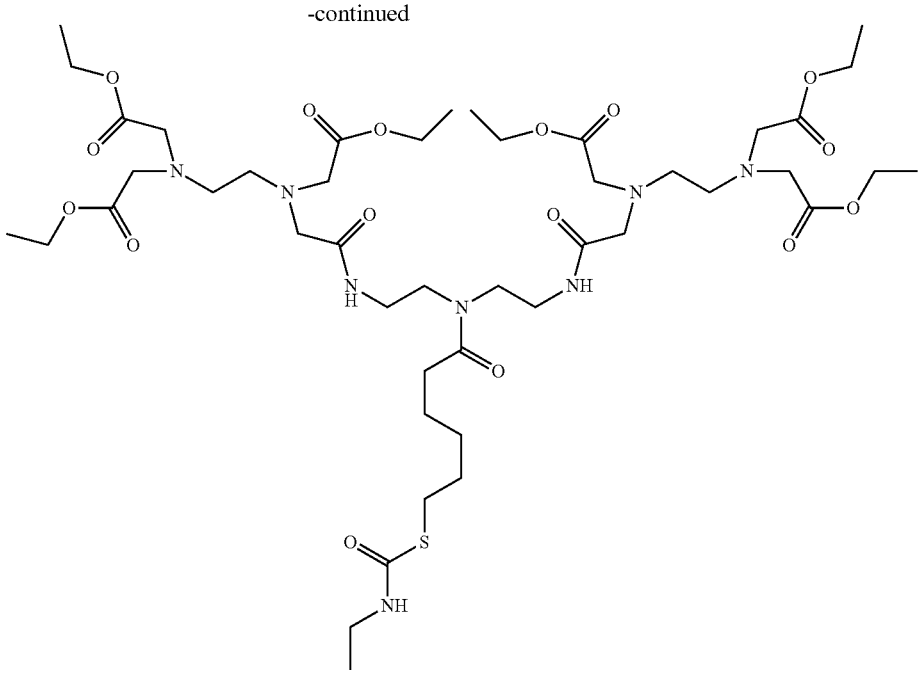

13

Synthesis of Fully Protected Pentadentate Dimer (13)

The synthetic route to obtain (10) was as described in example 1.

0.57 mmol of 6-Ethylcarbamoylsulfanyl-hexanoic acid (9) was dissolved in 3 ml dry Dichloromethane. 0.11 g (0.6 mmol) N-(3-Dimethylaminopropyl)-N'-ethylcarbodiimide hydrochloride and 0.09 g (0.64 mmol) 1-hydroxybenzotriazole hydrate was added and the reaction mixture was left at room temperature for 1 hr. The secondary amine (10) was dissolved in 1 ml dry Dichloromethane and 0.20 µl (1.4 mmol) Triethylamine. The amine solution was added to the reaction mixture dropwise and the reaction was left at room temperature for 17 hours. The reaction was monitored by LC-MS (3-100% Acetonitrile (0.05% TFA) in MilliQ water (0.05% TFA), 10 min, 0.5 ml/min, YMC-Pack Hydrosphere C18, S-3 µm, 120 Å, 50×4.6 mm i.d.).

The reaction mixture was washed with equal volume of distilled water. The aqueous phase was extracted twice with Dichloromethane. The organic phases were combined and washed with equal volume of 0.1 M Hydrogen chloride solution. The aqueous phase was extracted twice with Dichloromethane. The organic phases were combined and washed with equal volume of saturated Sodium chloride solution. The aqueous phase was extracted twice with Dichloromethane. The organic phases were combined and dried with Magnesium sulfate. The drying agent was removed by filtration and the supernatant was concentrated by vacuum to give crude product as amber oil. The crude was dissolved in 1.5 ml Acetonitrile and purified on semi-preparative HPLC (3-100% Acetonitrile (0.05% TFA) in MilliQ water (0.05% TFA) over 10 min, 50 ml/min, C18 column (ACE 10 AQ A 8257 250×30 mm i.d., 10 µm, 100 Å), UV-detection at 214 nm. Collected fractions were combined and concentrated under vacuum until a few milliliters remained. The solution was freeze-dried affording Pentadentate dimer as light yellow oil.

Protected Pentadentate Dimer (13)

Yield: 40%

ESI-MS: m/z=979.5 [M+H$^+$], 490.3 [M+2H$^+$], 1001.4 [M+Nc$^+$]

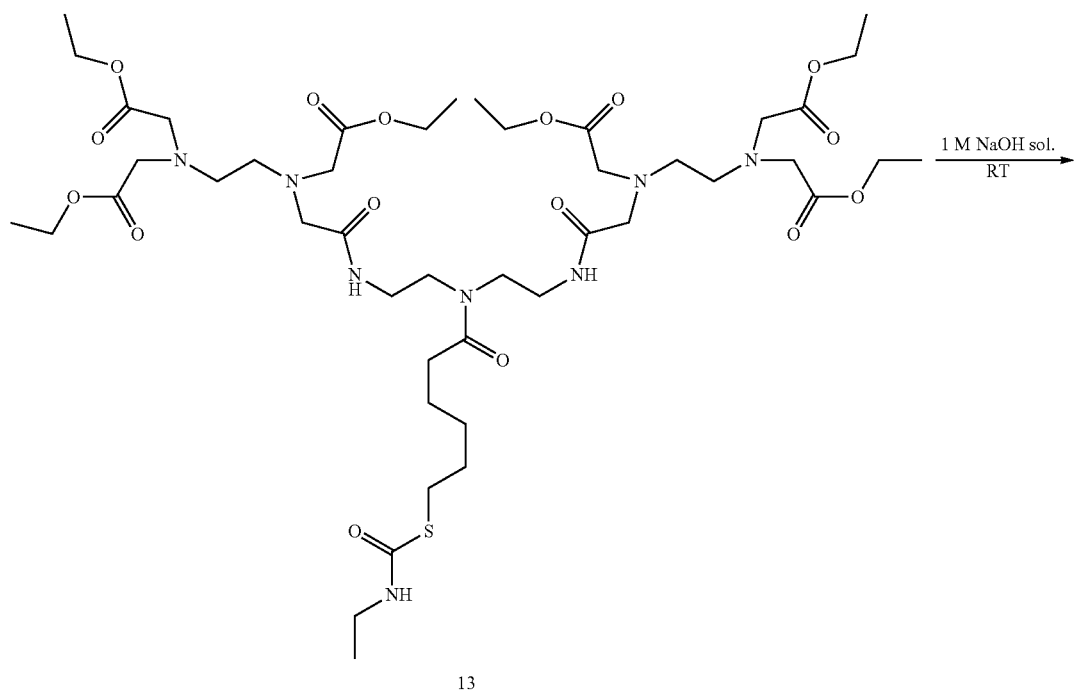
13
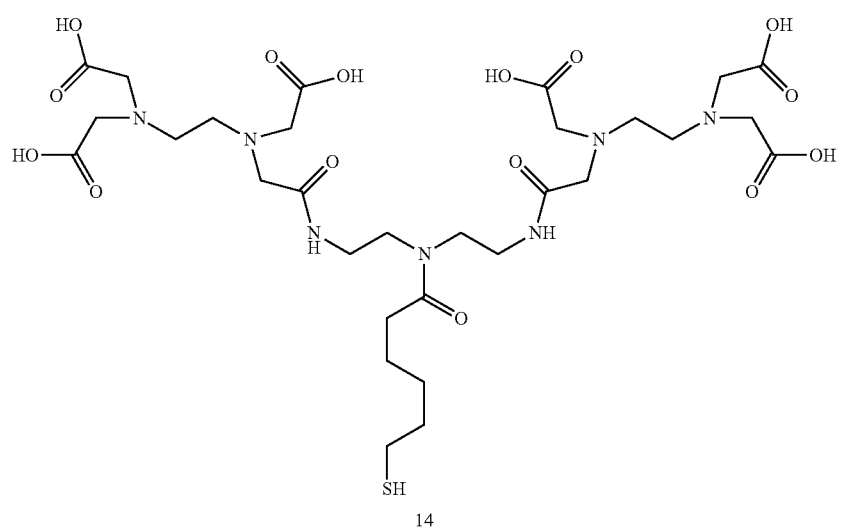
14

Synthesis of the Pentadentate Dimer Ligand (14)

The dimeric pentadentate ligand (14) from above (230 mg, 225 µmol) was put in a flask together with sodiumhydroxide (2 ml, 1M-solution) and magnetic stirring was begun. After three hours of stirring hydrochloric acid (1 ml, 1M-solution) was added to the flask and the solution transferred to a Falcon tube for coupling to allylactivated Sepharose™ HP media.

utes. The gel was then transferred to a glass filter and washed with distilled water (50 ml). The gel was drained and then transferred to the aforementioned Falcon tube with the pentadentate ligand solution (14). The pH was adjusted to 12 with sodiumhydroxide (1M-solution) and the tube was then put on a shaking table at 45° C., after about 30 minutes sodiumhydroxide (two drops of 1M-solution) was added to the tube which was then left on the shaking table over night.

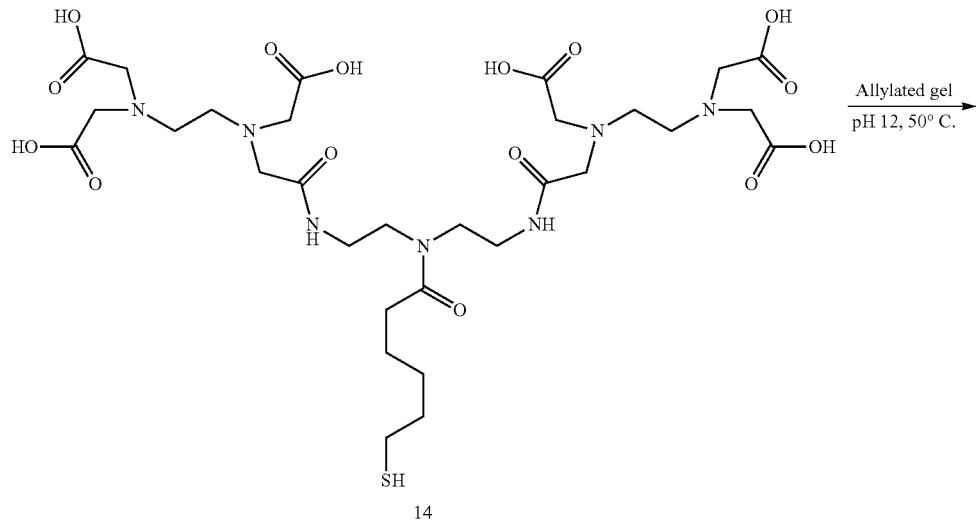

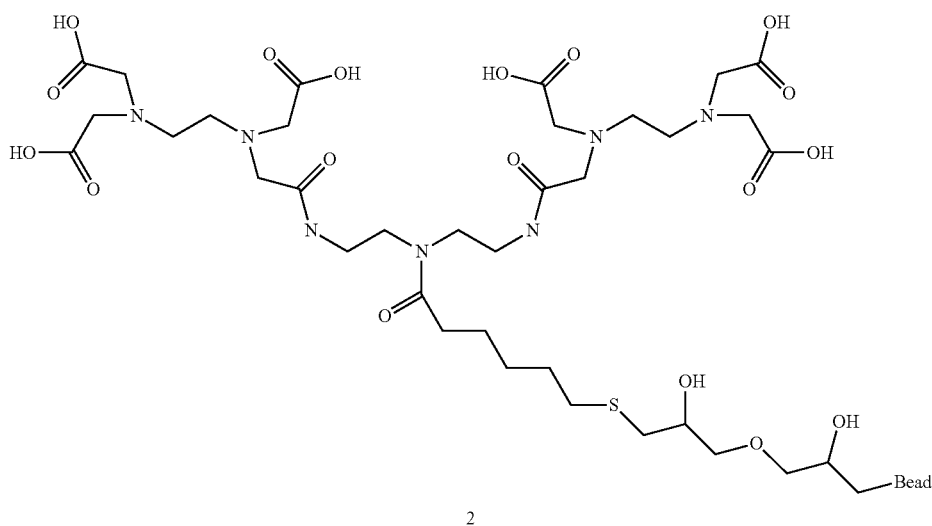

Coupling to Ally/Activated Sepharose™ HP Media to Afford a Resin with the Dimeric Pentadentate Chelator (2)

Drained allylactivated gel (130 µmol/mL) Sepharose™ HP resin (3 ml, 0.39 mol) was transferred to a beaker and water (approximately 50 ml) was added to the gel. During vigorous overhead stirring bromine water was added to a consistent yellow colour. After about 5 minutes of stirring sodium formiate was added until the gel slurry was completely discoloured and then left stirring for about 15 min- After about 20 hours the reaction was stopped and the resins washed with distilled water (4×50 ml) on a glass filter.

The dry weight of the resin was determined to 78 mg/ml by drying 0.5 ml of gel on a drying scale and the nitrogen content was then determined by elemental analysis to 1.91% which corresponds to a ligand content of 15 µmol/mL.

The $Ni^{2+}$-binding capacity, and loss Ni ions with EDTA was determined as described in Example 1:

$Ni^{2+}$-binding capacity (Qb10%): 43 µmol/ml resin.

Amount of Ni$^{2+}$ ions released in the NaCl wash: 4.5 µmol/ml

Ni$^{2+}$-content after NaCl wash: 38.5 µmol/ml resin.

The amount of Ni$^{2+}$ ions released in the 100 mM EDTA eluate after 2 hours of incubation was 1.9 µmol/ml (=4.9% of 38.5 µmol/ml).

EXAMPLE 3

Biacore Determination of Affinities for Binding of a Hexahistidine Peptide to Ni$^{2+}$-Charged Immobilized Pentadentate Chelators, Dimeric and Monomeric The dimeric pentadentate ligand from Example 1 was dissolved to 30 mM in 0.1 M NaOH; the corresponding monomeric pentadentate ligand was dissolved to 30 mM in 0.1 M NaOH.

Other materials (from GE Healthcare):

Sensor Chip CM5, BR-1000-14.

Biacore 2000 instrument

Amine Coupling Kit with EDC and NHS, BR-1000-50.

2-(2-pyridinyldithio)ethaneamine hydrochloride (PDEA), BR-1000-58.

HBS-P buffer: 10 mM HEPES pH 7.4, 0.15 M NaCl, 0.005% v/v Surfactant P20, BR-1003-68.

A nickel ion charging and recharging solution was prepared: 10 mM HEPES pH 7.4, 0.15 M NaCl, 0.005% v/v Surfactant P20, 500 µM NiSO$_4$.

Regeneration solution consisted of 10 mM HEPES, 0.15 M NaCl, 0.005% surfactant, and 100 mM imidazole, pH 7.4.

A 500 mM solution of the hexa-peptide "hex-his" (consisting of six histidines coupled to each other mimicking a (His)$_6$-tag) was prepared.

All other chemicals were of p.a. grade.

Both monomeric and dimeric pentadentate ligands were coupled in a Biacore 2000 instrument to Biacore CM5 sensor chip through thiol coupling using the standard kit from Biacore. The dimeric ligand was diluted in 0.1 M phosphate buffer, pH 7 to 1 mM and the monomeric ligand was diluted to 0.5 mM in the same buffer. At a flow rate of 10 µl/min, the flow cells were activated with 3 min of EDC/NHS mix and 4 min 80 mM PDEA in borate buffer, pH 8.5. The ligand solutions were then injected under a period of 30 min. The surfaces were then de-activated with 50 mM L-Cys/1 M NaCl under 4 min. The immobilisation level was estimated to 212 RU for dimeric ligand and 228 RU for the monomeric ligand.

For affinity measurements, hex-his was diluted to 2, 5, 10, 20, 50, 100, 200, 400 and 500 µM in HBS-P buffer. Ni ion recharging was done in the beginning of each cycle by injecting the Ni solution for 1 min. For the immobilised monomeric ligand, hex-his in different concentrations were injected for 6 min at a flow rate of 15 µL/min and for the immobilised dimeric ligand the injections were 15 min. The regeneration solution with 100 mM imidazole was applied after each cycle.

Affinity constants were determined from the relationship between the equilibrium binding level (Req) and the analyte concentration (C=concentration of hex-his). Two or more of the concentrations should be high enough so that the steady state binding levels Req approach saturation of the surface (Rmax). On a plot of Req against C, the $K_D$-value is equal to the concentration that gives 50% of the maximum response. If the range of concentrations is too small, the curvature of the Req against C plot cannot be determined satisfactorily and the calculated $K_D$ value will be uncertain.

Using the Biacore evaluation software BIAevaluation the affinity for the dimeric pentadentate ligand was calculated to be 14 µM.

For the monomeric pentadentate ligand, the equilibrium binding level (Req) was not reached with the analyte concentrations used. At the highest analyte concentration (500 µM) the Req was 85 RU. But it was clear that the Req was not approaching saturation. This means that the real Rmax will be larger than the measured 85 RU. Assuming an Rmax of 85 RU, the $K_D$ is at least 150 µM. Since the Rmax is higher than 85 RU, the $K_D$ of hex-his to immobilised monomeric ligand is higher than 150 µM.

The measurements of affinity of hex-his peptide to the immobilized ligands show that the monomeric ligand binds much weaker to hex-his peptide, with a dissociation constant $K_D$ at least 10 times higher than for the dimeric ligand.

EXAMPLE 4

Purification of the Histidine-Tagged Protein EGFP-(His)$_6$ using the Resin Obtained in Example 1-Comparison Between a Dimeric Chelator and the Corresponding Monomer EGFP-(His)$_6$ is a variant of green fluorescent protein; with a C-terminal hexahistidine-tag, an absorbance max at 490 nm and an approximate Mr of 28 000).

The Sepharose HP resin obtained in Example 1 was packed in a glass chromatography column to give a bed dimension of approx. 50×5 mm (≈1 ml).

Protein sample preparation: *E. coli* cells expressing no histidine-tagged proteins were suspended in an appropriate volume of a suitable lysis buffer containing protease inhibitor, and lysates were prepared by lysozyme treatment and sonication on ice, according to common laboratory practice. The lysates were clarified by high-speed centrifugation and filtration, giving extracts suitable for IMAC. Such extracts were mixed with known amounts of purified EGFP-(His)$_6$, for subsequent application to the test columns.

At room temperature (20-25° C.) and at a flow rate of 1.0 ml/min, a given volume of a mixture prepared as above, containing 5 mM imidazole, was applied to each of the columns (dimer column, and monomer column, respectively; pre-charged with Ni$^{2+}$ ions). Each column had previously been equilibrated with 20 mM sodium phosphate, 500 mM NaCl, 5 mM imidazole, pH 7.4. After column washing with 20 ml of the same buffer at 1 ml/min for the removal of unwanted binders in the sample, elution at 1 ml/min was accomplished with a linear imidazole gradient of 5 to 210 mM (17 ml). The gradient was formed by high-accuracy, on-line mixing from the above equilibration/wash buffer and an elution buffer containing the same components and also 500 mM imidazole, pH 7.4. The chromatography system used was an ÄKTAexplorer™.

With the column having a resin with the dimeric chelator, the gradient of 5-210 mM imidazole accomplished elution of a single peak without any shoulders, having volume-synchronized absorbances at 280 and 490 nm. The observed ratio between the two absorbances indicated a high purity of EGFP-(His)$_6$, as is known from our experience. Observation of the absorbance of the flow-through fraction and of the visible zone of the bound yellowish EGFP-(His)$_6$ in the column top, indicated that essentially all of the applied EGFP-(His)$_6$ had been bound, and that it later was completely eluted by the gradient.

With the 1-ml column (bed of approx. 50×5 mm) having a resin with a monomeric pentadentate chelator, corresponding to the dimeric one, and having approximately the same molar concentration and molar amount of coupled chelator (as determined by nitrogen analyses and by the Ni ion binding capacity which for the dimer resin was twice that of the monomer resin), essentially no EGFP-(His)$_6$ was bound. The applied EGFP-(His)$_6$ was instead seen in the sample flow-through fraction. Thus, the presence of 5 mM imidazole was sufficient to prevent the binding of EGFP-(His)$_6$ to the monomer resin, but not to the corresponding dimer resin, each resin with ligands at the same molar concentration. All the observations indicated the presence of a cooperative protein binding effect of the dimer chelator.

EXAMPLE 5

Figure 1B:
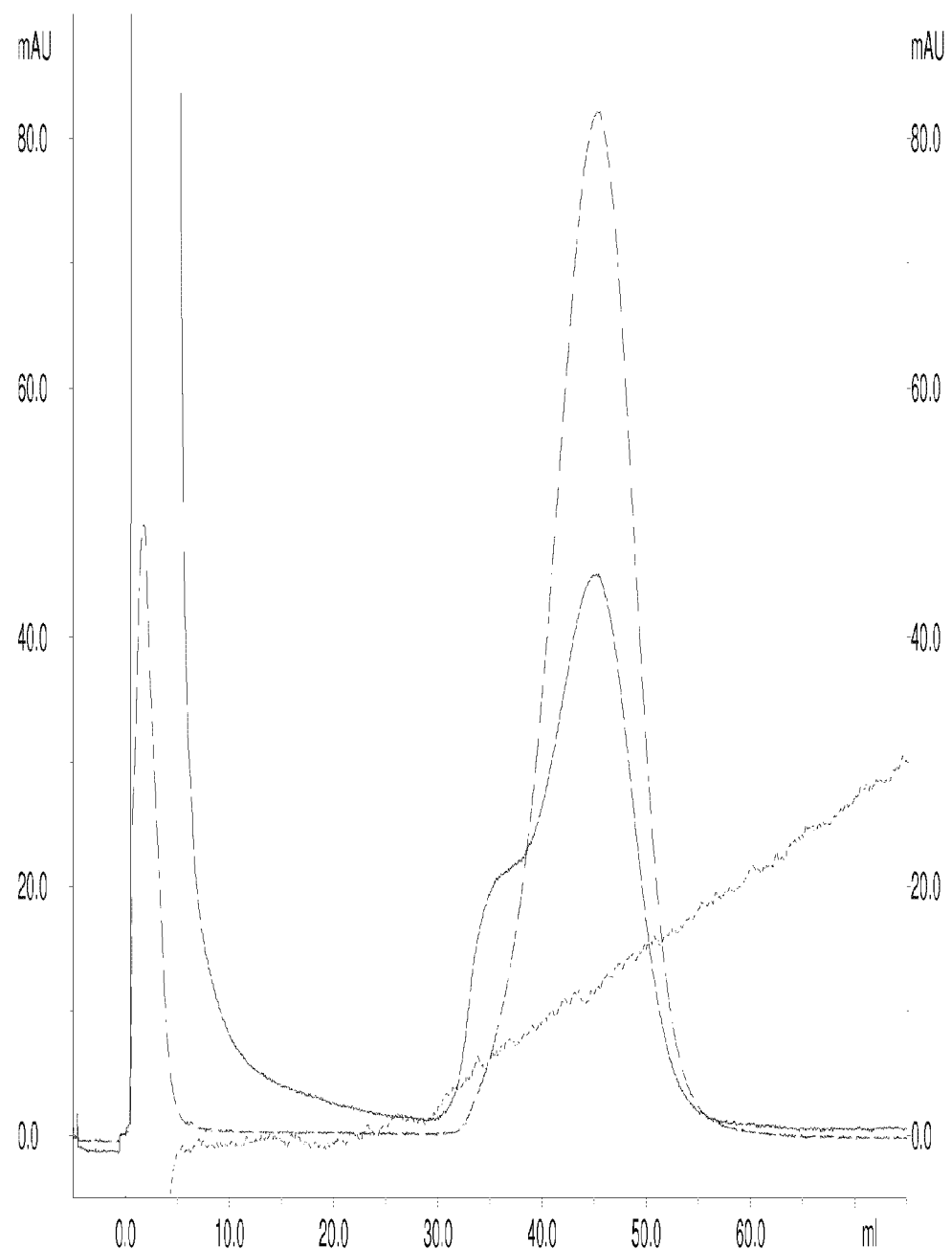

Purification of the Histidine-Tagged Protein EGFP-(His)$_6$ using the Resin Obtained in Example 2-Comparison Between a Dimeric Chelator and the Corresponding Monomer This example refers to FIG. 1.

EGFP-(His)$_6$ is a variant of green fluorescent protein; with a C-terminal hexahistidine-tag, an absorbance max at 490 nm and an approximate Mr of 28 000.

The Sepharose HP resin obtained in Example 2 was packed in a glass chromatography column to give a bed dimension of approx. 50×5 mm (≈1 ml).

The protein sample preparation was done as described in Example 4.

At room temperature (20-25° C.) and at a flow rate of 1.0 ml/min, a given volume of a mixture of E. coli extract and EGFP-(His)$_6$, prepared as in Example 4, containing no imidazole, was applied to each of the columns (pre-charged with Ni$^{2+}$ ions). Each column had previously been equilibrated with 20 mM sodium phosphate, 500 mM NaCl, pH 7.4. After column washing with 20 ml of the same buffer at 1 ml/min, for the removal of unwanted binders, elution at 1 ml/min was accomplished with a shallow linear imidazole gradient of 0 to 100 mM (80 ml). The gradient was formed by high-accuracy, on-line mixing from the above equilibration/wash buffer and an elution buffer containing the same components and also 500 mM imidazole, pH 7.4. The chromatography system used was an ÄKTAexplorer™.

With the column having the resin with the dimeric chelator, the imidazole gradient accomplished elution of a first (early) peak having absorbance at 280 nm, but none at 490 nm, showing that it contained only non-tagged E. coli proteins, and no EGFP-(His)$_6$. A larger, second peak then followed, with volume-syncronized absorbances both at 280 and 490 nm, and having a ratio between the two wavelengths that indicated a high purity of EGFP-(His)$_6$, as known from experience. Observation of the absorbance of the flow-through fraction and of the visible zone of the bound yellowish EGFP-(His)$_6$ in the column top, indicated that essentially all of the applied EGFP-(His)$_6$ had been bound, and that it later was completely eluted by the gradient.

With the 1-ml column (bed of approx. 50×5 mm) having a resin with a monomeric pentadentate chelator, corresponding to the dimeric one, and having approximately the same molar concentration and molar amount of coupled chelator (as determined by nitrogen analyses and by the Ni ion binding capacities), no separate early peak with only 280 nm absorbance was eluted. Instead, the slightly later eluted peak corresponding to EGFP-(His)$_6$ had a small 280-nm shoulder at the front, containing non-tagged components. The approximate area of that shoulder was about ⅓ of the area of the 280-nm peak in the run with the dimer resin. The elution volumes (from start of sample application to peak summit) of the peaks of EGFP-(His)$_6$ were 53 ml and 45 ml, respectively for the dimer and the monomer column.

These results indicated that the dimer resin bound more non-tagged E. coli components than the monomer resin, but also that it bound EGFP-(His)$_6$ more strongly since the elution volume of the EGFP-(His)$_6$ was considerably later for the dimer resin. The results also showed a better selectivity with the dimer resin, with respect to the separation (difference in elution volumes) between non-tagged components and the histidine-tagged EGFP-(His)$_6$. All these observations indicated the presence of a cooperative protein binding effect of the dimer chelator.

The invention claimed is:

1. A dimeric pentadentate chelator having the following general formula:

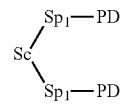

wherein PD is a pentadentate chelator having the formula:

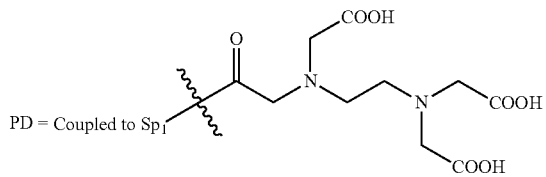

wherein $S_{p1}$ is 6-amino hexanoic acid;
wherein Sc is diethylenetriamine;
wherein an amine of $S_{p1}$ is coupled to PD to form an amide bond; and
wherein a carboxyl of $S_{p1}$ is coupled to a primary amine of Sc to form an amide bond.

2. The dimeric pentadentate chelator of claim 1, further comprising a group Q and having the following general formula:

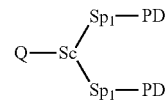

wherein Q is selected from a solid phase, a detection label, and a biomarker.

3. The dimeric pentadentate chelator of claim 2, wherein Q is a solid phase comprising a natural or synthetic polymer.

4. The dimeric pentadentate chelator of claim 2, wherein the solid phase is a porous chromatographic support.

5. The dimeric pentadentate chelator of claim 3, wherein Q is made of a cross-linked carbohydrate material selected from the group consisting of agarose, agar, cellulose, dextran, chitosan, konjac, carrageenan, gellan and alginate.

6. The dimeric pentadentate chelator of claim 3, wherein Q is made of synthetic polymers selected from the group consisting of styrene derivatives, divinylbenzene, acryl amides, acrylate esters, methacrylate esters, vinyl esters and vinyl amides.

7. The dimeric pentadentate chelator of claim 2, wherein Q comprises magnetic particles.

8. The dimeric pentadentate chelator of claim 2, wherein Q is a solid phase comprising a sensor surface.

9. The dimeric pentadentate chelator of claim 5, wherein Q is made of agarose.

* * * * *